United States Patent [19]

Pelrine

[11] Patent Number: 4,990,718

[45] Date of Patent: Feb. 5, 1991

[54] AROMATIC ALKYLATION WITH ALPHA-OLEFIN DIMER

[75] Inventor: Bruce P. Pelrine, Trenton, N.J.

[73] Assignee: Mobil Oil Corporation, Fairfax, Va.

[21] Appl. No.: 332,146

[22] Filed: Apr. 3, 1989

[51] Int. Cl.$^5$ .......................... C07C 2/64; C07C 15/10
[52] U.S. Cl. ...................................... 585/455; 585/467
[58] Field of Search ................................ 585/455, 467

[56] References Cited

U.S. PATENT DOCUMENTS

| | | | |
|---|---|---|---|
| 3,250,728 | 5/1966 | Miale et al. | 585/467 |
| 3,433,846 | 3/1969 | Adams et al. | 585/323 |
| 3,436,432 | 4/1969 | Mitsche | 585/467 |
| 3,442,965 | 5/1969 | Oldham | 585/455 |
| 3,478,113 | 11/1969 | Bray et al. | 585/323 |
| 3,484,498 | 12/1969 | Berg | 585/323 |
| 3,492,364 | 1/1970 | Jones et al. | 585/323 |
| 3,494,970 | 2/1970 | Pharis | 585/323 |
| 3,766,056 | 10/1973 | Young | 585/467 |
| 4,035,308 | 7/1977 | Schenach | 585/323 |
| 4,301,316 | 11/1981 | Young | 585/455 |
| 4,301,317 | 11/1981 | Young | 585/455 |
| 4,570,027 | 2/1986 | Boucher et al. | 585/455 |
| 4,731,497 | 3/1988 | Grey | 585/467 |

FOREIGN PATENT DOCUMENTS

| | | | |
|---|---|---|---|
| 1468982 | 5/1969 | Fed. Rep. of Germany | 585/455 |
| 42-23569 | 11/1967 | Japan | 585/455 |
| 44-11365 | 5/1969 | Japan | 585/455 |

*Primary Examiner*—Patrick P. Garvin
*Assistant Examiner*—E. D. Irzinski
*Attorney, Agent, or Firm*—Alexander J. McKillop; Charles J. Speciale; Malcolm D. Keen

[57] ABSTRACT

A process is disclosed for the production of novel monoalkylbenzenes or substituted benzenes by aromatics alkylation wherein the alkylation catalyst is an acidic shape selective metallosilicate catalyst and the alkylating agent is the olefins dimer by-product of the oligomerization of alpha-olefins in contact with reduced valence state solid chromium oxide catalyst on a porous support. The alkylated benzenes produced comprise those mono-alkylbenzenes wherein the alkyl group contains 12 to 28 carbon atoms and have high viscosity index, low pour point and low viscosity. They have a low degree of residual olefinic unsaturation and are useful as additives to thermally and oxidatively stabilize lubricant materials. The process comprises reacting benzene or substituted benzene with $C_6$-$C_{14}$ alpha-olefin olefinic dimer having a branch ratio of less than 0.19, or mixture of said dimers, in contact with acidic shape selective zeolite catalyst having large pore size.

16 Claims, No Drawings

AROMATIC ALKYLATION WITH ALPHA-OLEFIN DIMER

This invention relates to a process for the preparation of synthetic oils useful as lubricants, lubricant additives and insulating fluids. More particularly, the invention relates to a process for the monoalkylation of aromatic hydrocarbons with novel olefins obtained from the oligomerization of $C_6$–$C_{20}$ alpha-olefins where the alkylating agent is the alpha-olefin oligomerization dimer.

BACKGROUND OF THE INVENTION

It has been well established in the prior art that hydrocarbon oils possessing superior properties in applications such as low viscosity lubricants, insulating fluids for electrical transformers, additives for lubricants, and the like can be prepared by alkylation of aromatic compounds using using higher molecular weight olefins and olefinic oligomers.

Pellegrini, Jr. U.S. Pat. No. 4,238,343 discloses a synthetic oil composition useful as an insulating fluid in electrical apparatus comprising the mono or di-alkylation product from the alkylation of aromatics with oligomers containing at least 30 and up to 60 carbon atoms. The oligomers are prepared by Lewis acid catalysis by methods well known in the art. The alkylation reaction is conducted using conventional liquid Lewis acid catalyst and the degree of substitution is controlled by the aromatic to olefin mole ratio. Dimers are separated from oligomers and not included in the alkylation reaction.

Dressler et al. U.S. Pat. No. 4,604,491 discloses a synthetic oil composition for functional fluids such as lubricants, heat transfer fluids, vacuum pump oils, etc. The compositions comprise mono and polyalkylated naphthalenes prepared by the alkylation of naphthalene with alpha-olefins in contact with high silica zeolites. The alkyl substituent on naphthalene contains between 12 and 26 carbon atoms.

Yoshida et al. U.S. Pat. No. 4,714,794 discloses a synthetic oil composition comprising monoalkylated naphthalene obtained by alkylation of naphthalene with alkyl halide, alcohol or a straight chain mono-olefin having six to twenty four carbon atoms. The mole ratio of alpha to beta substitution on naphthalene is at least 1.0. The products exhibit high oxidation stability.

Recently, novel lubricant compositions (referred to herein as HVI-PAO) comprising polyalpha-olefins and methods for their preparation employing as catalyst reduced chromium on a silica support have been disclosed in U.S. patent applications Ser. No. 210,434 and 210,435 filed June 23, 1988, incorporated herein by reference. The process comprises contacting $C_6$–$C_{20}$ 1-alkene feedstock with reduced valence state chromium oxide catalyst on porous silica support under oligomerizing conditions in an oligomerization zone whereby high viscosity, high VI liquid hydrocarbon lubricant is produced having branch ratios less than 0.19 and pour point below $-15°$ C. The process is distinctive in that little isomerization of the olefinic bond occurs compared to known oligomerization methods to produce polyalpha-olefins using Lewis acid catalyst. Lubricants produced by the process cover the full range of lubricant viscosities and exhibit a remarkably high viscosity index (VI) and low pour point even at high viscosity. The assynthesized HVI-PAO oligomer has a preponderance of terminal olefinic unsaturation.

In the preparation of the novel HVI-PAO lubricant, alpha-olefin dimer containing olefinic unsaturation can be separated from the oligomerization reaction. The composition of the dimer mixture conforms to the unique specificity of the oligomerization reaction in that little double bond isomerization is found and shows a low branch ratio.

According, it is an object of the present invention to provide a process for the alkylation of aromatic hydrocarbons using HVI-PAO olefinic dimer.

Yet another object of the present invention is to provide a process for the monoalkylation of aromatic hydrocarbons with HVI-PAO dimer.

A further object of the present invention is to provide a method for increasing the thermal stability of lubricant compositions using monoalkylated aromatics derived from HVI-PAO dimer.

SUMMARY OF THE INVENTION

It has been discovered that novel monoalkylbenzenes or substituted benzenes can be produced by an aromatics alkylation process wherein the alkylation catalyst used is an acidic shape selective metallosilicate catalyst and the alkylating agent is the olefinic dimer by-product of the oligomerization of alpha-olefins in contact with reduced valence state solid chromium oxide catalyst on a porous support. The olefinic dimer is the by-product of an oligomerization process notable for the very low degree of double bond isomerization occurring during the reaction such that the oligomer hydrocarbons and dimer by-products produced show branch ratios below 0.19. The alkylated benzenes produced comprise those mono-alkylbenzenes wherein the alkyl group contains 12 to 28 carbon atoms.

It has been further discovered that the monoalkylbenzenes of the present invention have high viscosity indices, low pour point and low viscosity. They have a low degree of residual olefinic unsaturation and are useful as additives to thermally and oxidatively stabilize lubricant materials. They are, of themselves, useful as low viscosity lubricants.

More particularly, a process is disclosed for the production of aromatic hydrocarbon synthetic oil comprising the steps of:

contacting $C_6$–$C_{14}$ alpha olefin with a supported solid reduced metal oxide catalyst under oligomerization conditions at a temperature of about 90° to 250° C., said metal oxide comprising a lower valence form of at least one Group VIB metal to produce lubricant range hydrocarbon product oligomers having a branch ratio of about 0.10 to 0.19 and a viscosity index of at least about 130;

separating said oligomers and recovering $C_{12}$–$C_{28}$ olefinic dimer by-product by distillation; and reacting benzene or substituted benzene with said dimer, or mixture of said dimer, in contact with acidic shape selective metallosilicate catalyst under alkylating conditions whereby mono-alkylbenzenes containing $C_{12}$–$C_{28}$ alkyl group are produced.

DETAILED DESCRIPTION OF THE INVENTION

In the present invention aromatic hydrocarbons are alkylated with unique olefin dimers produced as by-product in the oligomerization of 1-alkenes in contact with reduced chromium oxide on silica support. A characteristic of the novel oligomerization reaction from which the by-product dimers used as alkylating agent in the present invention are produced is the production of mixtures of dialkyl vinylidenic and 1,2 dialkyl or trialkyl mono-olefin oligomers (referred to herein as HVI-PAO oligomers), as determined by infra-red and NMR analysis.

In general, the HVI-PAO oligomers have the following regular head-to-tail structure where n is preferably 0 to 17, terminating in olefinic unsaturation:

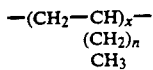

with some head-to-head connections. The HVI-PAO process produces a surprisingly simpler and useful dimer compared to the dimer produced by 1-alkene oligomerization with $BF_3$ or $AlCl_3$ as commercially practiced. Typically, in the present invention it has been found that a significant proportion of unhydrogenated dimerized 1-alkene, or alpha-olefin, has a vinylidenyl structure as follows:

where $R_1$ and $R_2$ are alkyl groups representing the residue from the head-to-tail addition of 1-alkene molecules. For example, the by-product dimer from 1-decene oligomerization according to the HVI-PAO process, which can be used as alkylating olefin in the present invention, has been found to contain three major components, as determined by GC. Based on $^{13}C$ NMR analysis, the unhydrogenated components were found to be 8-eicosene, 9-eicosene, 2-octyldodecene and 9-methyl-8 or 9-methyl-9-nonadecene.

Olefins suitable for use as starting material in the preparation of olefinic HVI-PAO oligomers and the by-product dimer used as starting material in the present invention include those olefins containing from 6 to about 14 carbon atoms such as 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-octene to 1-dodecene and more preferably 1-decene, or mixtures of such olefins.

HVI-PAO oligomers of alpha-olefins used in this invention have a low branch ratio of less than 0.19 and superior lubricating properties compared to the alpha-olefin oligomers with a high branch ratio, as produced in all known commercial methods.

This class of unsaturated HVI-PAO alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The support material usually has high surface area and large pore volumes with average pore size of 40 to about 350 angstroms. The high surface area are beneficial for supporting large amount of highly dispersive, active chromium metal centers and to give maximum efficiency of metal usage, resulting in very high activity catalyst. The support should have large average pore openings of at least 40 angstroms, with an average pore opening of >60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250° to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the reaction products and by-products are calculated from the weight fractions of methyl groups obtained by infrared methods, published in *Analytical Chemistry*, Vol 25, No. 10, p. 1466 (1953).

$$\text{Branch ratio} = \frac{\text{wt fraction of methyl group}}{1 - (\text{wt fraction of methyl group})}$$

The unique olefinic dimers used as alkylating agent in the present invention are produced as by-product of the HVI-PAO oligomerization reaction. Typically, in the production of HVI-PAO oligomer lubricant base stock, the oligomerization reaction mixture is separated from the catalyst and separated by vacuum distillation to remove unreacted alpha-olefin and lower boiling by-products of the oligomerization reaction, such as alpha-olefin dimer. This provides a lubricant basestock of suitably high volatility and viscosity. While other methods known to those skilled in the art, such as solvent extraction, may be used to separate the alpha-olefin dimer by-product, distillation is preferred.

In the process of the present invention to produce alkylated aromatics, particularly mono-alkylbenzenes, by alkylation with aforenoted dimer, suitable aromatic hydrocarbon starting materials include benzene, mono and di-alkylbenzenes, halobenzenes, alkoxybenzenes, carboxy and carbalkoxy benzenes, phenol, catechol, acetanilide, acetophenone, and the like. Preferred aromatics include benzene, toluene, chlorobenzene and anisole.

The alkylation reaction of the present invention is conducted by contacting a mixture of olefinic dimer and aromatic hydrocarbon with a solid shape selective acidic metallosilicate catalyst having a large pore size. The reaction may be conducted at a temperature between 0 and 300° C., but preferably between 160° and 200° C. The reaction pressure can be between 1 psig and 1000 psig, but is preferably about 400 psig. The liquid hourly space velocity (LHSV) based on catalyst can be between 0.01 and 10, but is preferably between about 0.4 and 0.6.

The alkylation reaction can be conducted with or without a solvent. Useful solvents include nitrobenzene, tetrahydrofuran, perchlorobenzene and all such generally higher boiling solvents inert in the alkylation reaction. However, it is preferable to conduct the reaction in the absence of added solvent and more preferable to employ an excess of aromatic hydrocarbon reactant as solvent. The process of the present invention can be carried out to produce mono-alkylbenzenes using a mole ratio of reactant benzenes to olefinic dimer alkylating agent of between 50:1 and 0.5:1, but preferably the reaction is carried out using a mole ratio of benzenes to dimer alkylating agent of between 5:1 and 1:1. The reaction can be carried out in any vessel suitable for the reaction between fluid alkylating agent and benzenes with solid catalyst. Preferably, the reaction is conducted in a fixed bed reactor or a continuous stirred tank reactor but may be effectively carried out in a batch reactor.

Surprisingly, the process of the present invention leads to essentially mono alkylation of aromatic hydrocarbon with olefinic dimer when the alkylation is carried out using acidic shape selective metallosilicate catalyst such as aluminosilicate zeolite. The shape selective characteristics of zeolite catalysts are well known to those skilled in the art and in the present invention such shape selectivity is deemed to have a determining influence on the surprising limitation of the reaction products to essential monoalkylates. The application of shape-selective catalysis is discussed in "Industrial Application of Shape Selective Catalysis" by N. Y. Chen and W. E. Garwood in Catal. Rev.-Sci. Eng., 28(2&3),185–264 (1986), incorporated herein by reference in its entirety.

Zeolites of interest to shape selective catalysis are divided into three major groups according to their pore/channel systems. These systems include 8-membered oxygen ring systems, 10-membered oxygen ring systems and dual pore systems including 12-membered oxygen ring openings. In general, they are referred to as small, medium or large pore size zeolites proceeding from 8 to 12 membered ring systems. The systems are more completely described in Atlas of Zeolite Structures Types, International Zeolite Assoc., Polycrystal Book Service, Pittsburg, 1978.

Zeolites useful as catalysts in the present invention include all natural or synthetic acidic large pore size zeolites, typically with a pore size of about 6.4 to 7.5 Angstoms. Particularly useful catalysts include the acidic form of ZSM-4, ZSM-12, ZSM-20, Faujasite X & Y with pore size of 7.4 Angstroms, Cancrinite, Gmelinite, Mazzite, Mordenite and Offretite. A preferred catalyst is Faujasite Y.

The following examples are presented to illustrate the novel oligomerization reaction and oligomers produced therefrom which provides as a by-product the olefinic dimer used as alkylating agent in the present invention. The dimer is separated by distillation from the oligomerization reaction mixture.

EXAMPLE 1

Catalyst Preparation and Activation Procedure 1.9 grams of chromium (II) acetate ($Cr_2(OCOCH_3)_4 2H_2O$)(5.58 mmole) (commercially obtained) is dissolved in 50 cc of hot acetic acid. Then 50 grams of a silica gel of 8–12 mesh size, a surface area of 300 $m^2/g$, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The catalyst prepared in Example 1 (3.2 g ) is packed in a ⅜" stainless steel tubular reactor inside an $N_2$ blanketed dry box. The reactor under $N_2$ atmosphere is then heated to 150° C. by a single-zone Lindberg furnace. Prepurified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |

-continued

| Sample | Prerun | 1 | 2 | 3 |
|---|---|---|---|---|
| VI | 159 | 151 | 142 | 143 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

The following examples of the instant invention are presented merely for illustration purposes and are not intended to limit the scope of the present invention.

EXAMPLE 5

Five grams of an ammonium Faujacite Y zeolite is placed into a fixed bed reactor. The catalyst is bound with 35% silica. The reactor is heated in air to 538° C. and maintained at this temperature for 12 hours. The ammonium Y zeolite is transformed to the hydrogen or acidic Y form. A feed comprised of benzene and by-product $C_{20}$ olefinic dimer from the oligomerization of 1-decene in the mole ratio of 5:1 benzene to dimers is passed over the catalyst at 400 psig. The initial reaction temperature is 160° C. at an LHSV of 0.4. At these reaction conditions 88.1% of the dimers are reacted, according to gas chromatographic analysis. After distillation at 220° C. and 5 mm Hg, the product has the properties presented in Table 1.

EXAMPLE 6

Using the same feed and catalyst as in Example 5, reaction was carried out at 200° C. and 0.6 LHSV. Dimer conversion is 92.8%, accordingly to gas chromatographic analysis. The product properties are presented in Table 1.

Infrared analysis of the mono-alkylbenzenes confirmed that the structures are alkylbenzenes. IR spectra of a model compound, 1-phenyldodecane, when compared to the products made by this method is found to be identical.

Gas chromatographic analysis of the products further shows the presence of $C_{26}$ mono-alkyl benzenes. No disubstituted products are noted by GC analysis.

The following elemental analysis and molecular weight determinations are consistent with mono alkyl substitution:

| | % Carbon | % Hydrogen | M.W. |
|---|---|---|---|
| Example 5 | 87.23 | 13.38 | 385 |
| Example 6 | 87.09 | 12.87 | 379 |
| Calculated (monoalkyl) | 87.15 | 12.85 | 358 |

TABLE 1

| Example | 5 | 6 |
|---|---|---|
| Temperature, °C. | 160 | 200 |
| Pressure, psig | 400 | 400 |
| LHSV | 0.4 | 0.6 |
| % Conversion of Dimer | 88.1 | 92.8 |
| ALKYLATE PROPERTIES | | |
| KV, 40° C. | 17.80 | 15.47 |
| KV, 100° C. | 3.86 | 3.47 |
| Viscosity Index | 108.7 | 99.4 |
| Bromine Number | 2.4 | 4.4 |
| Pour Point, °C. | −35.7 | −37.5 |

It has been discovered that the products of the present invention are useful as additives to mineral oil and synthetic oils when added to those oils in small but sufficient amounts. Lubricants are often formulated with additives to enhance properties for specific applications. The more commonly used additives include oxidation inhibitors, rust inhibitors, metal passivators, antiwear agents, extreme pressure additives, pour point depressants, detergent-dispersants, viscosity index (VI) improvers, foam inhibitors and the like. This aspect of lubricant arts is specifically described in Kirk-Othmer "Encyclopedia of Chemical Technology", 3rd edition, Vol. 14, pp 477–526, incorporated herein by reference. Alkylated aromatics are known in the prior art as lubricant additives for their antiwear properties, thermal and oxidative stability as disclosed in U.S. Pat. Nos. 4,211,665, 4,238,343, 4,604,491 and 4,714,7944.

Although the present invention has been described with preferred embodiments and examples, it is to be understood that modifications and variations may be resorted to without departing from the spirit and scope of this invention, as those skilled in the art will readily understand. Such modifications and variations are considered to be within the purview and scope of the following claims.

What is claimed is:

1. A process for the production of mono-alkylbenzenes containing $C_{12}$–$C_{28}$ alkyl group from alpha-olefin dimer, comprising,
    contacting a $C_6$–$C_{14}$ alpha olefin with a supported solid reduced metal oxide catalyst under oligomerization conditions at a temperature of about 90° to 250° C., said metal oxide comprising a lower valence form of at least one Group VIB metal to produce lubricant range hydrocarbon product oligomers having a branch ratio of about 0.10 to 0.19 and a viscosity index of at least about 130 and a $C_{12}$–$C_{28}$ olefin dimer;
    separating the oligomers and recovering the dimer,
    reacting benzene or substituted benzene with the dimer, or mixture of said dimers, in contact with acidic shape selective metallosilicate catalyst under alkylating conditions whereby said mono-alkylbenzenes are produced.

2. The process of claim 1 wherein said metallosilicate catalyst comprises acidic aluminosilicate zeolite-type catalyst containing large pore size.

3. The process of claim 2 wherein said catalyst comprises acidic zeolite containing pore size of about 7.4 Angstroms.

4. The process of claim 1 wherein said catalyst comprises acidic X or Y Faujasite.

5. The process of claim 1 wherein said supported solid reduced metal oxide catalyst comprises carbon monoxide reduced chromium oxide and said support comprises silica.

6. The process of claim 1 wherein said alpha-olefins are taken from the group consisting essentially of 1-hexene, 1-octene, 1-decene, 1-dodecene and 1-tetradecene.

7. The process of claim 1 wherein said dimer comprises 1-decene dimer containing 20 carbon atoms.

8. The process of claim 1 wherein said monoalkyl benzenes comprise $C_{20}$ alkylbenzenes having a bromine number below 5, viscosity index greater than 90 and pour point below $-30°$ C.

9. The process of claim 1 wherein said alkylating conditions comprise temperature between 0° and 300° C., pressure between 1 and 1000 psig and liquid hourly space velocity between 0.01 and 10.

10. The process of claim 1 wherein said alkylating conditions comprise temperature between about 160° and 200° C., pressure about 400 psig and liquid hourly space velocity between about 0.4 and 0.6.

11. A process for the production of aromatic hydrocarbon lubricant or lubricant additive, comprising the steps of:

contacting $C_6$–$C_{14}$ alpha olefin with a supported solid reduced metal oxide catalyst under oligomerization conditions at a temperature of about 90° to 250° C., said metal oxide comprising a lower valence form of at least one Group VIB metal to produce lubricant range hydrocarbon product oligomers having a branch ratio of about 0.10 to 0.19 and a viscosity index of at least about 130;

separating said oligomers and recovering $C_{12}$–$C_{28}$ olefinic dimer fraction thereof by distillation; and reacting benzene or substituted benzene with said dimer, or mixture of said dimers, in contact with acidic shape selective metallosilicate catalyst under alkylating conditions whereby mono-alkylbenzenes containing $C_{12}$–$C_{28}$ alkyl group are produced.

12. The process of claim 11 wherein said metallosilicate catalyst comprises acidic zeolite containing pore size of about 7.4 Angstroms.

13. The process of claim 11 wherein said metallosilicate catalyst comprises acidic X or Y Faujasite.

14. The process of claim 11 wherein said supported solid reduced metal oxide catalyst comprises carbon monoxide reduced chromium oxide and said support comprises silica.

15. The process of claim 11 wherein said dimer comprises 1-decene dimer containing 20 carbon atoms having a branch ratio less than 0.19.

16. The process of claim 11 wherein said monoalkyl benzenes comprise $C_{20}$ alkylbenzenes having a bromine number below 5, viscosity index greater than 90 and pour point below $-30°$ C.

* * * * *